United States Patent
Keyser et al.

(10) Patent No.: US 9,592,253 B1
(45) Date of Patent: Mar. 14, 2017

(54) EXTENDED USE ZIRCONIUM SILICATE COMPOSITIONS AND METHODS OF USE THEREOF

(71) Applicant: ZS PHARMA, INC., Coppell, TX (US)

(72) Inventors: Donald Jeffrey Keyser, Southlake, TX (US); Alvaro F. Guillem, Lantana, TX (US)

(73) Assignee: ZS PHARMA, INC., Coppell, TX (US)

( * ) Notice: Subject to any disclaimer, the term of this patent is extended or adjusted under 35 U.S.C. 154(b) by 0 days.

(21) Appl. No.: 14/883,428

(22) Filed: Oct. 14, 2015

(51) Int. Cl.
  *A61K 33/24* (2006.01)
  *A61K 9/16* (2006.01)
  *B01J 39/08* (2006.01)
  *C01B 39/02* (2006.01)

(52) U.S. Cl.
  CPC .......... *A61K 33/24* (2013.01); *A61K 9/16* (2013.01); *B01J 39/085* (2013.01); *C01B 39/02* (2013.01)

(58) Field of Classification Search
  CPC . A61K 33/24; A61K 9/16; B01J 39/08; C01B 39/00; C01B 39/02
  See application file for complete search history.

(56) References Cited

U.S. PATENT DOCUMENTS

| | | | |
|---|---|---|---|
| RE21,224 E | 10/1939 | Kinzie | |
| 3,947,279 A | 3/1976 | Hudecek | |
| 4,581,141 A | 4/1986 | Ash | |
| 4,943,545 A | 7/1990 | Chang et al. | |
| 5,015,453 A | 5/1991 | Chapman | |
| 5,338,527 A | 8/1994 | Lambert | |
| 5,518,707 A | 5/1996 | Bedard et al. | |
| 5,624,652 A | 4/1997 | Aldcroft et al. | |
| 5,888,472 A | 3/1999 | Bem et al. | |
| 5,891,417 A | 4/1999 | Bem et al. | |
| 5,910,299 A | 6/1999 | Carluccio et al. | |
| 6,007,790 A | 12/1999 | Bedard et al. | |
| 6,099,737 A | 8/2000 | Sherman et al. | |
| 6,146,613 A | 11/2000 | Anglerot et al. | |
| 6,332,985 B1 | 12/2001 | Sherman et al. | |
| 6,379,641 B1 | 4/2002 | Bedard et al. | |
| 6,579,460 B1 | 6/2003 | Willis et al. | |
| 6,596,254 B1 | 7/2003 | Nenoff et al. | |
| 6,689,335 B1 | 2/2004 | Bringley et al. | |
| 6,814,871 B1 | 11/2004 | Bem et al. | |
| 7,297,319 B2 | 11/2007 | Vitale-Rojas et al. | |
| 7,566,432 B2 | 7/2009 | Wong | |

(Continued)

FOREIGN PATENT DOCUMENTS

| | | |
|---|---|---|
| EP | 0 982 785 A1 | 3/2000 |
| ES | 2 304 890 A1 | 10/2008 |
| GB | 2 038 301 A | 7/1980 |

OTHER PUBLICATIONS

Ash, "Sorbents in Treatment of Uremia: A Short History and a Great Future," Seminars in Dialysis, vol. 22, No. 6 (Nov.-Dec. 2009), pp. 615-622.

(Continued)

*Primary Examiner* — Kortney L Klinkel
(74) *Attorney, Agent, or Firm* — Arent Fox LLP

(57) ABSTRACT

The present invention relates to zirconium silicate compositions having a lead content that is below 0.6 ppm and methods of manufacturing zirconium silicate at reactor volumes exceeding 200-L with a lead content below 1.1 ppm. The lead content of the zirconium silicate of this invention are within the levels that are considered acceptable for extended use given the dose requirements for zirconium silicate.

30 Claims, 5 Drawing Sheets

Dark = ZrO3 (oct), Light = SiO2 (tet), Cations not shown

(56) References Cited

U.S. PATENT DOCUMENTS

| | | | |
|---|---|---|---|
| 7,967,984 | B2 | 6/2011 | Midorikawa et al. |
| 8,093,350 | B2 | 1/2012 | Jung et al. |
| 8,431,502 | B2 | 4/2013 | Dejneka et al. |
| 8,802,152 | B2 | 8/2014 | Keyser et al. |
| 8,808,750 | B2 | 8/2014 | Keyser et al. |
| 8,877,255 | B2 | 11/2014 | Keyser et al. |
| 2004/0005575 | A1 | 1/2004 | Rosen et al. |
| 2004/0105895 | A1 | 6/2004 | Ash |
| 2007/0128424 | A1 | 6/2007 | Omori et al. |
| 2007/0202180 | A1 | 8/2007 | Liversidge et al. |
| 2007/0269499 | A1 | 11/2007 | Hen et al. |
| 2008/0241092 | A1 | 10/2008 | Charmot et al. |
| 2009/0186093 | A1 | 7/2009 | Liu et al. |
| 2010/0104527 | A1 | 4/2010 | Mansky et al. |
| 2010/0322847 | A1 | 12/2010 | Xiao et al. |
| 2012/0070468 | A1 | 3/2012 | Bedard et al. |
| 2012/0213847 | A1 | 8/2012 | Keyser et al. |
| 2012/0259141 | A1 | 10/2012 | Yilmaz et al. |
| 2013/0123096 | A1 | 5/2013 | Xiao et al. |
| 2013/0129611 | A1 | 5/2013 | Maurer et al. |
| 2013/0202524 | A1 | 8/2013 | Maurer et al. |
| 2013/0259949 | A1 | 10/2013 | Cope et al. |
| 2013/0296159 | A1 | 11/2013 | Feyen et al. |

OTHER PUBLICATIONS

Ash, Cation Exchangers as Oral Sorbents for Ammonium and Potassium: PSS, ZP and ZS (Zirconium Silicate), Clarian Arnett Health, Wellbound and HemoCleanse Inc., Lafayette, IN, (2007), ASAIO Innovation Conference, Chicago (25 pages).

Baussy et al., Bull. Soc. fr. Mineral. Cristallogr. (1974) vol. 97, pp. 433-444, English abstract only considered.

Bem et al., "Synthesis and Characterization of a New Family of Microporous Zirconium Silicates," (1999), Materials Research Society, Symposium Procedures, vol. 549, pp. 73-78.

Bortun et al., Chem. Mater. (1997) vol. 9, No. 8, pp. 1854-1864.

Braun et al., "Ammonium Removal With a Novel Zirconium Silicate," Presentation. (2001), ASAIO Conference (16 pages).

Chukanov et al., Minerals as Advanced Materials II (2012) pp. 167-179 (S.V. Krivovichev (ed)).

Chukanov et al., Russian Journal of Physical Chemistry B (2011) vol. 5, No. 2, pp. 278-283.

Chukanov et al., Russian Journal of Physical Chemistry B (2011) vol. 5, No. 2, pp. 284-289.

Clearfield et al., Journal of Molecular Structure (1998) vol. 470, pp. 207-213.

Dunn et al., American Mineralogist (1977) vol. 62. pp. 416-420.

Ferreira et al., Chem. Mater. (2001) vol. 13, pp. 355-363.

Ferreira et al., Inorganica Chimica Acta (2003) vol. 356. pp. 19-26.

Ferreira et al., Journal of Solid State Chemistry (2010) vol. 183, pp. 3067-3072.

Fewox et al., J. Phys. Chem. A (2008) vol. 112, pp. 2589-2597.

Fundaments of Physics (c) 1997 John Wiley & Sons, Inc., USA, pp. 947-949, section 37-9 X-Ray Diffraction.

Henderson, Lee W., Seminars in Dialysis (2012) vol. 25, No. 3, pp. 320-325.

International Search Report and Written Opinion of PCT/US2012/024727 mailed Aug. 7, 2012.

International Search Report and Written Opinion of PCT/US2013/045219 mailed Nov. 8, 2013.

International Search Report and Written Opinion of PCT/US2013/066207 mailed Feb. 14, 2014.

Lopes et al., Quim. Nova. (2008) vol. 31, No. 2, pp. 321-325.

Navascues et al., Chemical Engineering and Processing (2008) vol. 47, pp. 1139-1149.

Navascues et al., Desalination (2006) vol. 199, pp. 368-370.

Pekov et al., Cryst. Report (2010) vol. 55, No. 6, pp. 1031-1040.

Pertierra et al., Inorganic Chemistry Comm. (2002) vol. 5, pp. 824-828.

Poojary et al., Inorg. Chem. (1997) vol. 36, pp. 3072-3079.

Rocha et al., Chem. Comm. (1998) 1269-1270.

Yong-Nan et al., Chem. Res. Chinese U. (2002) vol. 18, No. 4, pp. 380-384.

ZS Pharma Products website from Sep. 9, 2010 (http://web.archive.orglweb/20100906160415/http://zspharma.com/products, accessed Mar. 28, 2014 via archive.org).

ZS Pharma Welcome website Sep. 6, 2010 (http://webarchive.org/web/20100906213849/http://zspharma.com/index.php?format=feed&type=atom, accessed Mar. 28, 2014 via archive.org) containing a comment from Dan Olson from Jan. 9, 2010.

ZS-9 Particle Size Distribution Analysis Report (4 pages), Nov. 4, 2009.

Dark = ZrO3 (oct), Light = SiO2 (tet), Cations not shown

US 9,592,253 B1

EXTENDED USE ZIRCONIUM SILICATE COMPOSITIONS AND METHODS OF USE THEREOF

BACKGROUND OF THE INVENTION (i) Field of the Invention

The present invention relates to novel microporous zirconium silicate compositions that are formulated to remove toxins, e.g., potassium ions or ammonium ions, from the gastrointestinal tract at an elevated rate without causing undesirable side effects. The compositions are manufactured to exhibit desired characteristics for the long term administration to treat or prevent the relapse or occurrence of certain conditions, i.e., hyperkalemia.

(ii) Description of the Related Art

Acute hyperkalemia is a serious life threatening condition resulting from elevated serum potassium levels. Potassium is a ubiquitous ion, involved in numerous processes in the human body. It is the most abundant intracellular cation and is critically important for numerous physiological processes, including maintenance of cellular membrane potential, homeostasis of cell volume, and transmission of action potentials. Its main dietary sources are vegetables (tomatoes and potatoes), fruit (oranges, bananas) and meat. The normal potassium levels in plasma are between 3.5-5.0 mmol/l with the kidney being the main regulator of potassium levels. The renal elimination of potassium is passive (through the glomeruli) with active reabsorption in the proximal tubule and the ascending limb of the loop of Henle. There is active excretion of potassium in the distal tubules and the collecting duct, both of which processes are controlled by aldosterone.

Increased extracellular potassium levels result in depolarization of the membrane potential of cells. This depolarization opens some voltage-gated sodium channels, but not enough to generate an action potential. After a short period of time, the open sodium channels inactivate and become refractory, increasing the threshold to generate an action potential. This leads to impairment of the neuromuscular-, cardiac- and gastrointestinal organ systems, and this impairment is responsible for the symptoms seen with hyperkalemia. Of greatest concern is the effect on the cardiac system, where impairment of cardiac conduction can lead to fatal cardiac arrhythmias such as a systole or ventricular fibrillation. Because of the potential for fatal cardiac arrhythmias, hyperkalemia represents an acute metabolic emergency that must be immediately corrected.

Hyperkalemia may develop when there is excessive production of serum potassium (oral intake, tissue breakdown). Ineffective elimination, which is the most common cause of hyperkalemia, can be hormonal (as in aldosterone deficiency), pharmacologic (treatment with ACE-inhibitors or angiotensin-receptor blockers) or, more commonly, due to reduced kidney function or advanced cardiac failure. The most common cause of hyperkalemia is renal insufficiency, and there is a close correlation between degree of kidney failure and serum potassium (S-K) levels. In addition, a number of different commonly used drugs cause hyperkalemia, such as ACE-inhibitors, angiotensin receptor blockers, potassium-sparing diuretics (e.g. amiloride, spironolactone), NSAIDs (such as ibuprofen, naproxen, celecoxib), heparin and certain cytotoxic and/or antibiotic drugs (such as cyclosporin and trimethoprim). Finally, beta-receptor blocking agents, digoxin or succinylcholine are other well-known causes of hyperkalemia. In addition, advanced degrees of congestive heart disease, massive injuries, burns or intravascular hemolysis cause hyperkalemia, as can metabolic acidosis, most often as part of diabetic ketoacidosis.

Symptoms of hyperkalemia are somewhat non-specific and generally include malaise, palpitations and muscle weakness or signs of cardiac arrhythmias, such as palpitations, brady-tachycardia or dizziness/fainting. Often, however, the hyperkalemia is detected during routine screening blood tests for a medical disorder or after severe complications have developed, such as cardiac arrhythmias or sudden death. Diagnosis is obviously established by S-K measurements.

Treatment depends on the S-K levels. In milder cases (S-K between 5-6.5 mmol/l), acute treatment with a potassium binding resin (Kayexalate®), combined with dietary advice (low potassium diet) and possibly modification of drug treatment (if treated with drugs causing hyperkalemia) is the standard of care; if S-K is above 6.5 mmol/l or if arrhythmias are present, emergency lowering of potassium and close monitoring in a hospital setting is mandated. The following treatments are typically used:

Kayexalate®, a resin that binds potassium in the intestine and hence increases fecal excretion, thereby reducing S-K levels. However, as Kayexalate® has been shown to cause intestinal obstruction and potential rupture. Further, diarrhea needs to be simultaneously induced with treatment. These factors have reduced the palatability of treatment with Kayexalate®.

Insulin IV (+glucose to prevent hypoglycemia), which shifts potassium into the cells and away from the blood.

Calcium supplementation. Calcium does not lower S-K, but it decreases myocardial excitability and hence stabilizes the myocardium, reducing the risk for cardiac arrhythmias.

Bicarbonate. The bicarbonate ion will stimulate an exchange of K+ for Na+, thus leading to stimulation of the sodium-potassium ATPase, dialysis (in severe cases).

The only pharmacologic modality that actually increases elimination of potassium from the body is Kayexalate®; however, due to the need to induce diarrhea, Kayexalate® cannot be administered on a chronic basis, and even in the acute setting, the need to induce diarrhea, combined with only marginal efficacy and a foul smell and taste, reduces its usefulness.

The use of zirconium silicate or titanium silicate microporous ion exchangers to remove toxic cations and anions from blood or dialysate is described in U.S. Pat. Nos. 6,579,460, 6,099,737, 6,332,985 and U.S. 2004/0105895, each of which is incorporated herein in their entirety. Additional examples of microporous ion exchangers are found in U.S. Pat. Nos. 6,814,871, 5,891,417, and 5,888,472, each of which is incorporated herein in their entirety.

The inventors have found that known zirconium silicate compositions may exhibit undesirable effects when utilized in vivo for the removal of potassium in the treatment of hyperkalemia. Specifically, the inventors found that administration of zirconium silicate molecular sieve compositions is associated with an incidence of mixed leukocyte inflammation, minimal acute urinary bladder inflammation and the observation of unidentified crystals in the renal pelvis and urine in animal studies, as well as an increase in urine pH. The inventors addressed these problems by controlling particle size and sodium content of the zirconium silicate compositions. See U.S. Pat. Nos. 8,802,152 and 8,808,750, each of which is incorporated herein in their entirety.

Further, known zirconium silicate compositions have had issues with crystalline impurities and undesirably low cation exchange capacity. The reduction of more soluble forms of zirconium silicate is important to reduce or eliminate the systemic absorption of zirconium or zirconium silicate. The inventors addressed this issue by controlling production conditions in a way that essentially eliminates ZS-8 from the composition, resulting in undetectable levels of ZS-8. See U.S. Pat. No. 8,877,255.

The inventors have found that certain zirconium silicate compositions are useful for long term use, for example, in the treatment of conditions associated with elevated levels of serum potassium. The use of zirconium silicate compositions in long term treatment regimens requires careful control of impurities, particularly lead, in the composition. For example, the FDA sets the acceptance criteria for lead in compositions for extended use at 5 micrograms per day. The inventors have found that zirconium silicates produced using known methods in industrial quantities contain approximately 1 to 1.1 ppm or more of lead. Even when zirconium silicate was prepared in smaller batches at higher purity (i.e., using reagent grade starting materials available from Sigma-Aldrich), the level of lead was found to be 0.6 ppm or more. Because zirconium silicate treatments utilize doses ranging from 5 to 45 grams per day, reduction in the level of lead is necessary. The present invention relates to compositions of zirconium silicate having lead content within an acceptable range necessitated by the daily doses of zirconium silicate.

SUMMARY OF THE INVENTION

The present invention relates to cation exchange compositions comprising a zirconium silicate of formula (I):

$$A_p M_x Zr_{1-x} Si_n Ge_y O_m \qquad (I)$$

where
A is a potassium ion, sodium ion, rubidium ion, cesium ion, calcium ion, magnesium ion, hydronium ion or mixtures thereof,
M is at least one framework metal, wherein the framework metal is hafnium (4+), tin (4+), niobium (5+), titanium (4+), cerium (4+), germanium (4+), praseodymium (4+), terbium (4+) or mixtures thereof,
"p" has a value from about 1 to about 20,
"x" has a value from 0 to less than 1,
"n" has a value from about 0 to about 12,
"y" has a value from 0 to about 12,
"m" has a value from about 3 to about 36 and $1 \leq n+y \leq 12$,
wherein the composition exhibits a lead content below 0.6 ppm. Preferably, the lead content ranges from 0.1 and 0.6 ppm, more preferably from 0.3 to 0.5 ppm, and most preferably from 0.3 to 0.45 ppm. In one embodiment, the lead content is 0.38 ppm. The present invention also relates to manufacturing zirconium silicate at reaction volumes at or exceeding 200-L where the lead content is below 1.1 ppm. In this embodiment, the lead content ranges from 0.1 and 1.1 ppm, more preferably from 0.3 to 0.5 ppm, and most preferably from 0.3 to 0.45 ppm.

In addition to having a desired level of lead impurity, the composition may exhibit one or more properties that make it desirable as an orally ingested ion trap. In one aspect, the zirconium silicate composition may have a potassium exchange capacity exceeding 2.3 meq/g, preferably ranging from 2.3 to 3.5 meq/g, more preferably within the range of 3.05 and 3.35 meq/g, and most preferably about 3.2 meq/g. In one embodiment, 7% of the particles in the composition have a diameter less than 3 microns. In other embodiments less than 0.5% of the particles in the composition have a diameter less than 1 microns. Preferably, the sodium content is below 12% by weight, and more preferably 9% or less by weight. The zirconium silicate preferably exhibits an XRD diffractogram having the two highest peaks occurring at approximately 15.5 and 28.9, with the highest peak occurring at 28.9. The material is preferably ZS-9, or predominately ZS-9, having a pH ranging from 7 to 9 and a potassium loading capacity between 2.7 and 3.7 mEq/g, and most preferably approximately 3.5.

The invention also relates to methods of administration of the above zirconium silicate compositions. In one preferred embodiment, the zirconium silicate compositions are administered over a period of more than 5 consecutive days.

DETAILED DESCRIPTION OF THE INVENTION

The inventors have discovered novel zirconium silicate molecular sieve absorbers that address the need for extended use compositions having a low impurity profile. The zirconium silicate compositions meet the performance criteria for previously described zirconium silicate compositions, but also exhibit reduced impurities, particularly lead, which make the compositions suitable for extended use.

Figure 1:
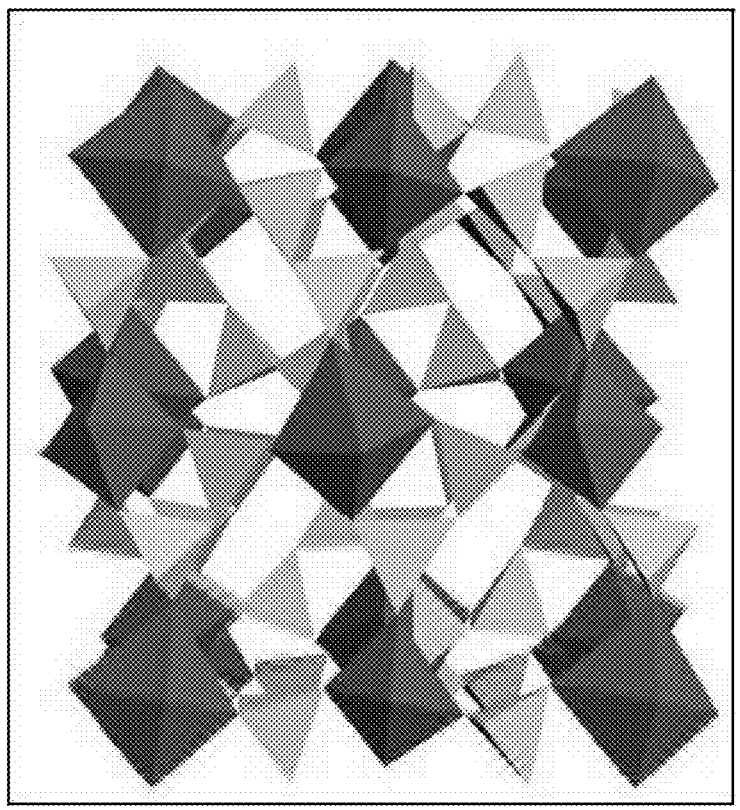
FIG. 1 is a polyhedral drawing showing the structure of zirconium silicate $Na_{2.19}ZrSi_{3.01}O_{9.11}*2.71H_2O$ (MW 420.71)
Figure 2:
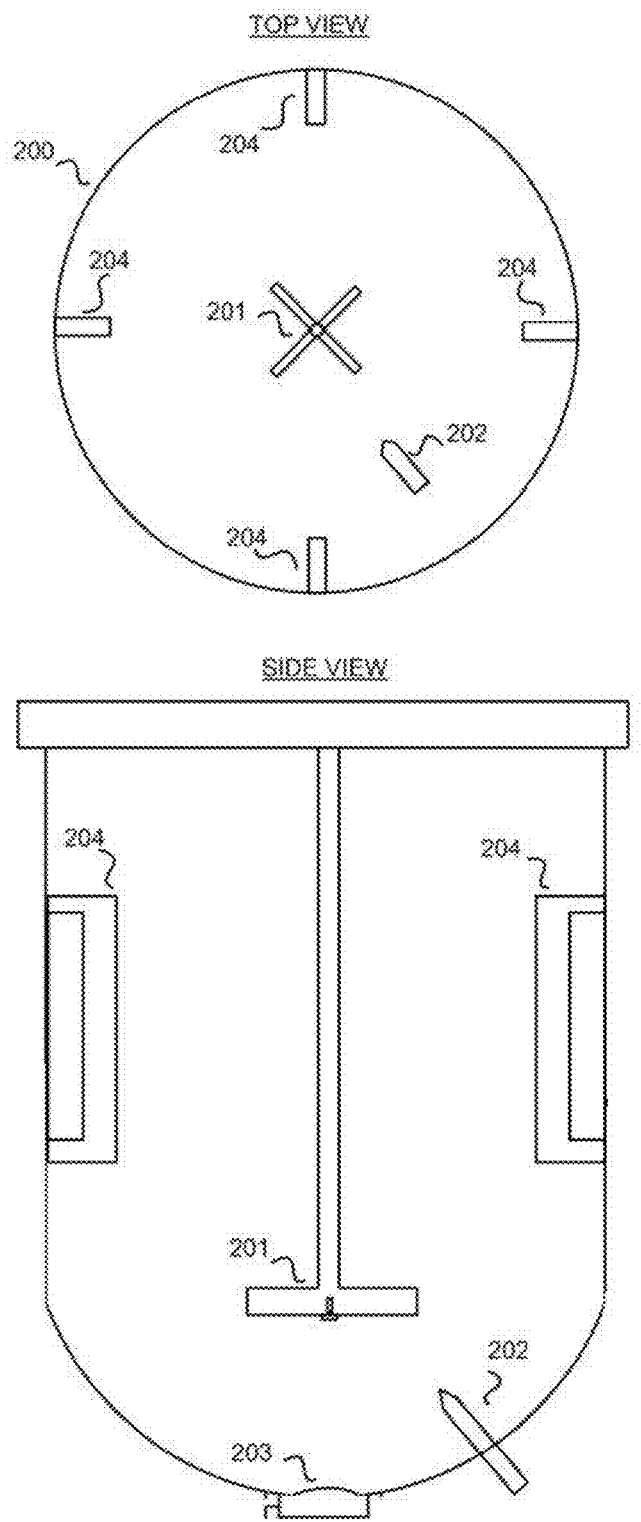
FIG. 2 shows a schematic drawing of a reaction vessel with baffles for production of zirconium silicate.

The inventors have designed a reactor for larger-scale production of high purity, high-KEC ZS-9 crystals. See U.S. Pat. Nos. 8,802,152; 8,808,750; and 8,877,255. The reactor 200 has baffle structures 204 on its sidewalls, which in combination with the agitator 201 provide significant lift and suspension of the crystals during reaction and the creation of high purity, high KEC ZS-9 crystals. FIG. 2. The improved reactor can also include a cooling or heating jacket for controlling the reaction temperature during crystallization in addition to the baffle structures 204. Preferably the reactor has a volume of at least 20-L, more preferably 200-L, 500-L, 2000-L, or 5000-L, and within the range of 200-L to 30,000-L.

Figure 3:
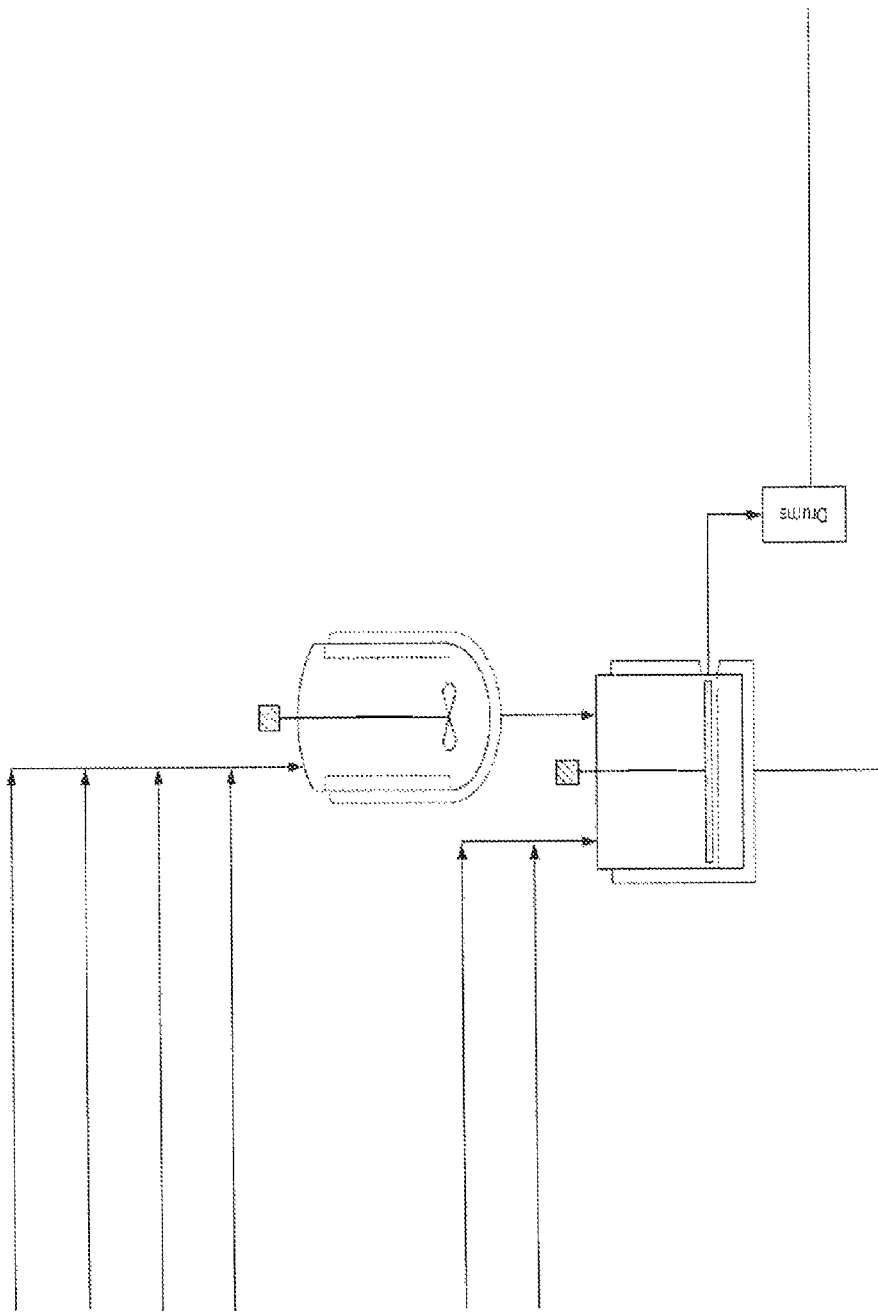
FIG. 3 shows a diagram of the processing equipment used to produce zirconium silicate.

The process flow for production of zirconium silicate is shown in FIG. 3. To a reactor are added a silicate source. The prior processes capable of manufacturing zirconium silicate having the desired characteristics for oral administration used sodium silicate as a source of silicate. The process also uses 50% NaOH solution, water and zirconium acetate which are charged to the reactor shown in FIG. 3. Also shown is a dryer in which the raw zirconium silicate product is fed. The zirconium silicate is cleaned, protonated and dried in the drier to produce the desired zirconium silicate along with aqueous waste material.

As discussed below in Example 2, the silicate source is colloidal silica (Ludox®) rather than sodium silicate. The inventors found that replacing the sodium silicate in known processes for manufacturing high quality zirconium silicates is ineffective. The present invention is based on the inventors' discovery that the reactor should not be initially charged with the colloidal silica but instead added to previously mixed sodium hydroxide and water. In addition, the agitation rate must be increased after addition of the colloidal silica for at least twenty minutes in order to break silica bonds and obtain a well mixed solution. Additional aspects of the inventive process can be understood by reference to Example 2 below.

The zirconium silicate according to the invention exhibits a lead content below 1 ppm. More preferably, the lead content ranges from 0.1 and 0.8 ppm, more preferably from 0.3 to 0.6 ppm, and most preferably from 0.3 to 0.45 ppm. In one embodiment, the lead content is 0.38 ppm.

Comparative Example 1

High capacity ZS-9 crystals were prepared in accordance with the following representative example.

The reactants were prepared as follows. A 22-L Morton flask was equipped with an overhead stirrer, thermocouple, and an equilibrated addition funnel. The flask was charged with deionized water (8,600 g, 477.37 moles). Stirring was initiated at approximately 145-150 rpm and sodium hydroxide (661.0 g, 16.53 moles NaOH, 8.26 moles $Na_2O$) was added to the flask. The flask contents exothermed from 24° C. to 40° C. over a period of 3 minutes as the sodium hydroxide dissolved. The solution was stirred for an hour to allow the initial exotherm to subside. Sodium silicate solution (5,017 g, 22.53 mole SO2, 8.67 moles $Na_2O$) was added. The sodium silicate was available from Sigma-Aldrich. To this solution, by means of the addition funnel, was added zirconium acetate solution (2,080 g, 3.76 moles $ZrO_2$) over 30 min. The resulting suspension was stirred for an additional 30 min.

The mixture was transferred to a 5-G Parr pressure vessel Model 4555 with the aid of deionized water (500 g, 27.75 moles). The reactor was fitted with a cooling coil having a serpentine configuration to provide a baffle-like structure within the reactor adjacent the agitator. The cooling coil was not charged with heat exchange fluid as it was being used in this reaction merely to provide a baffle-like structure adjacent the agitator.

The vessel was sealed and the reaction mixture was stirred at approximately 230-235 rpm and heated from 21° C. to 140-145° C. over 7.5 hours and held at 140-145° C. for 10.5 hours, then heated to 210-215° C. over 6.5 hours where the maximum pressure of 295-300 psi was obtained, then held at 210-215° C. for 41.5 hours. Subsequently, the reactor was cooled to 45° C. over a period of 4.5 hours. The resulting white solid was filtered with the aid of deionized water (1.0 KG). The solids were washed with deionized water (40 L) until the pH of the eluting filtrate was less than 11 (10.54). A representative portion of the wet cake was dried in vacuo (25 inches Hg) overnight at 100° C. to give 1,376 g (87.1%) of ZS-9 as a white solid.

As discussed in the '152 patent, the specific reactor configuration and process conditions of this Example demonstrated that higher capacity zirconium silicates could be achieved. For example, capacities ranging from 3.8-3.9 meq/g were achieved relative to prior processes that only achieved capacities in the range of 1.7-2.3 meq/g.

The inventors have found, however, that material produced in accordance with this Example exhibits a lead content of 0.6 ppm. The lead content is determined using Inductively Coupled Plasma-Mass Spectrometry (ICP-MS). The samples were prepared with a 0.1 g weighed portion mixed with 0.5 mL hydrofluoric acid, 2 mL nitric acid, 1 mL hydrochloric acid, and 1 mL purified water. The sample is digested using a closed-vessel microwave system at a maximum of 200° C. until the material appeared dissolved. After cooling, internal standard solution was added and dilution with purified water to 50 g produced solutions for ICP-MS.

The main contribution of lead to the zirconium silicate product comes from the reactants zirconium acetate and sodium silicate. This example illustrates that even when reagent grade materials (sodium silicate, zirconium acetate) are used as reactants, the level of lead can exceed that which is acceptable.

Example 2

This example illustrates the production of zirconium silicate from the reaction of sodium silicate and zirconium acetate in a 500-L reactor. Sodium silicate (148.8 kg) and water (100.1 kg) were added to a 500-L reactor and stirred at a rate of 200 rpm. Sodium hydroxide (37.7 kg) was added and the remaining water (100.2 kg) was added. The agitation rate was lowered to 80 rpm and zirconium acetate (62.0 kg) was added along with water (49.4 kg) and the reactor was allowed to mix for 25-35 minutes. The reactor was heated to react the materials 210±5° C. for ≥48 hours at 140 rpm. The resultant material was protonated to a pH of 4.75 to 5.25 and dried to a moisture content of ≤5.0%.

The composition has a volume weighted mean of 21.8 microns and a surface weighted mean of 13.56 microns. The material contains less than 0.05% of its volume under 1 micron, and less than 1.41% under 3 microns. The resultant material exhibits the characteristic XRD plot for ZS-9. There are undetectable levels of ZS-8 as shown by the absence of please within the range of 5-10 2-theta. As described in the inventors' prior patents, this material having a reduced amount of particulate fines and lacking soluble forms of zirconium silicate (ZS-8) is suitable for oral administration, for example in the treatment of hyperkalemia.

The inventors have found, however, that material produced in accordance with this example exhibits levels of lead above the suitable level given the required dosing of the drug. See Table 2 below. In particular, the resulting product was found to have a level of lead of 1.0 ppm. The main contribution of lead to the zirconium silicate product comes from the reactants zirconium acetate (0.28 ppm) and sodium silicate (0.38 ppm). Forms of zirconium acetate having lower levels of lead are unavailable on a commercial scale. Although other forms of silicate, colloidal silica, were found having undetectable levels of lead, colloidal silica is unsuitable in the above process for reaction with zirconium acetate to form zirconium silicate. The inventors have found that the level of lead in the final product tends to be higher when the level of lead in the reagents is uncontrolled, which can be the case with bulk suppliers of these reagents. Similar levels of lead on the order of 1-1.1 ppm were observed when the reaction was conducted at a scale of 200-L and 500-L in reactor volume.

Example 3

This example illustrates the production of zirconium silicate from the reaction of colloidal silica and zirconium acetate in a 500-L reactor. The inventors found that in order to react colloidal silica with zirconium acetate, the process must include additional steps and different agitation rates. For example, the colloidal silica process requires a step of increased agitation (200 rpm) for ≥20 minutes to break silica bonds and obtain a well mixed solution. The inventors found that through this process the level of lead could be lowered below 1 ppm, and as shown below can be lowered to 0.38 ppm in a 500-L reactor.

Sodium hydroxide (97.2 kg) is mixed with 84.5 kg of water and agitated at 150 rpm while 108.8 kg colloidal silica (Ludox®) is added. Agitation continues at the same rate while 10.5 kg water is used to clear the colloidal silica from the charge line into the reactor. Once the colloidal silica is charged to the reactor, the agitation is increased to 200 rpm for at least 20 minutes to break the silica bonds and obtain a well mixed solution. The agitation is reduced to 100 rpm while additional 52.9 kg water is added, and then increased to 200 rpm for at least five more minutes.

The agitation is then decreased to 150 rpm while 81.0 kg of zirconium acetate is added over a period of approximately 30 minutes. Water (62.8 kg) is added and stirring continued for about 30 minutes prior to heating.

The reactor is heated to 210° C. as quickly as possible while mixing at 150 rpm. The reactor is maintained at 210±5° C. for at least 36 hours. Upon completion, the material is protonated twice to a pH within the range of 4.75 to 5.25. The material is dried to a moisture content of less than 5% by heating at 160° C. for 30 minutes.

Figure 4:
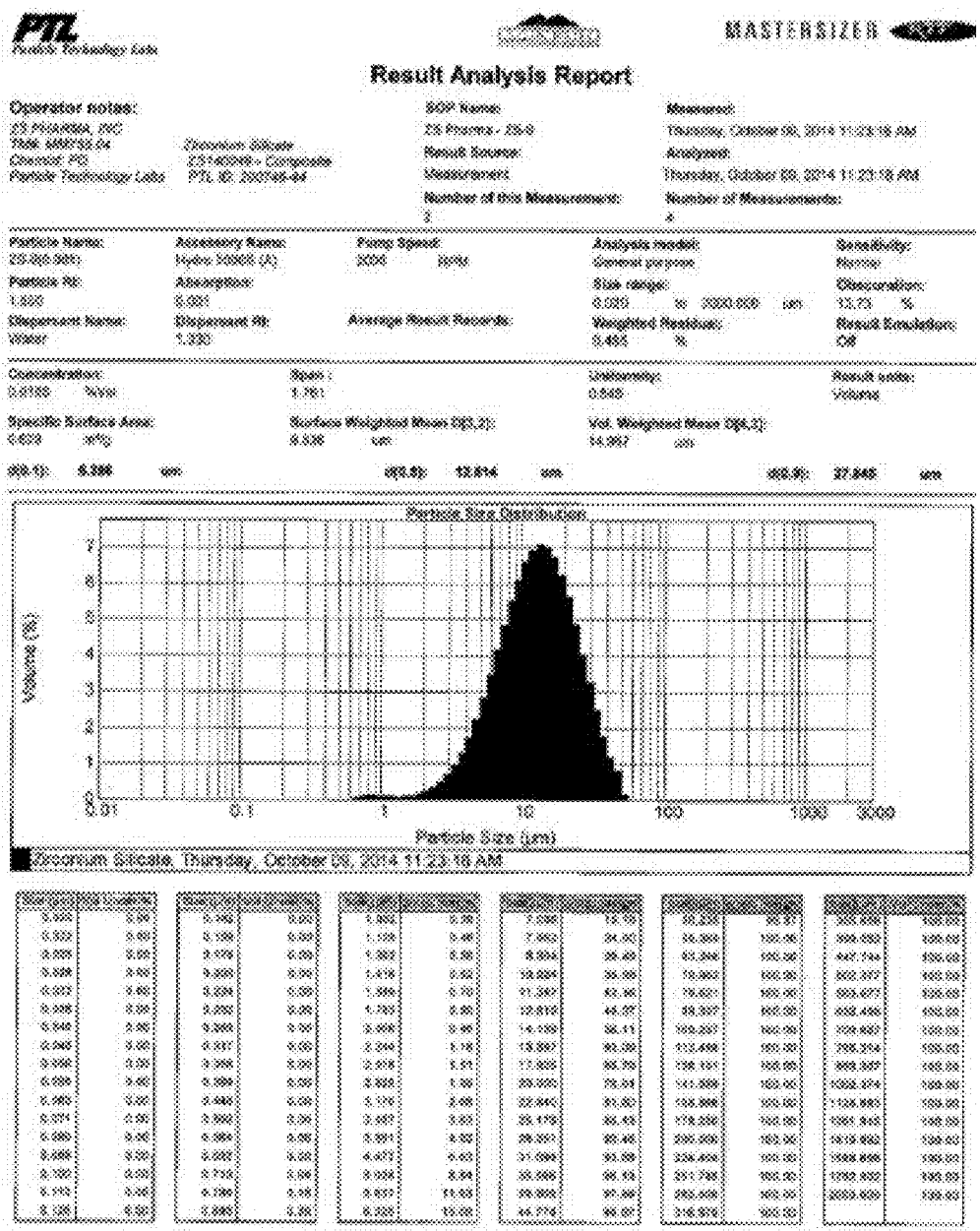
FIG. 4 shows particle size distribution of a zirconium silicate prepared according to Example 3.
Figure 5:
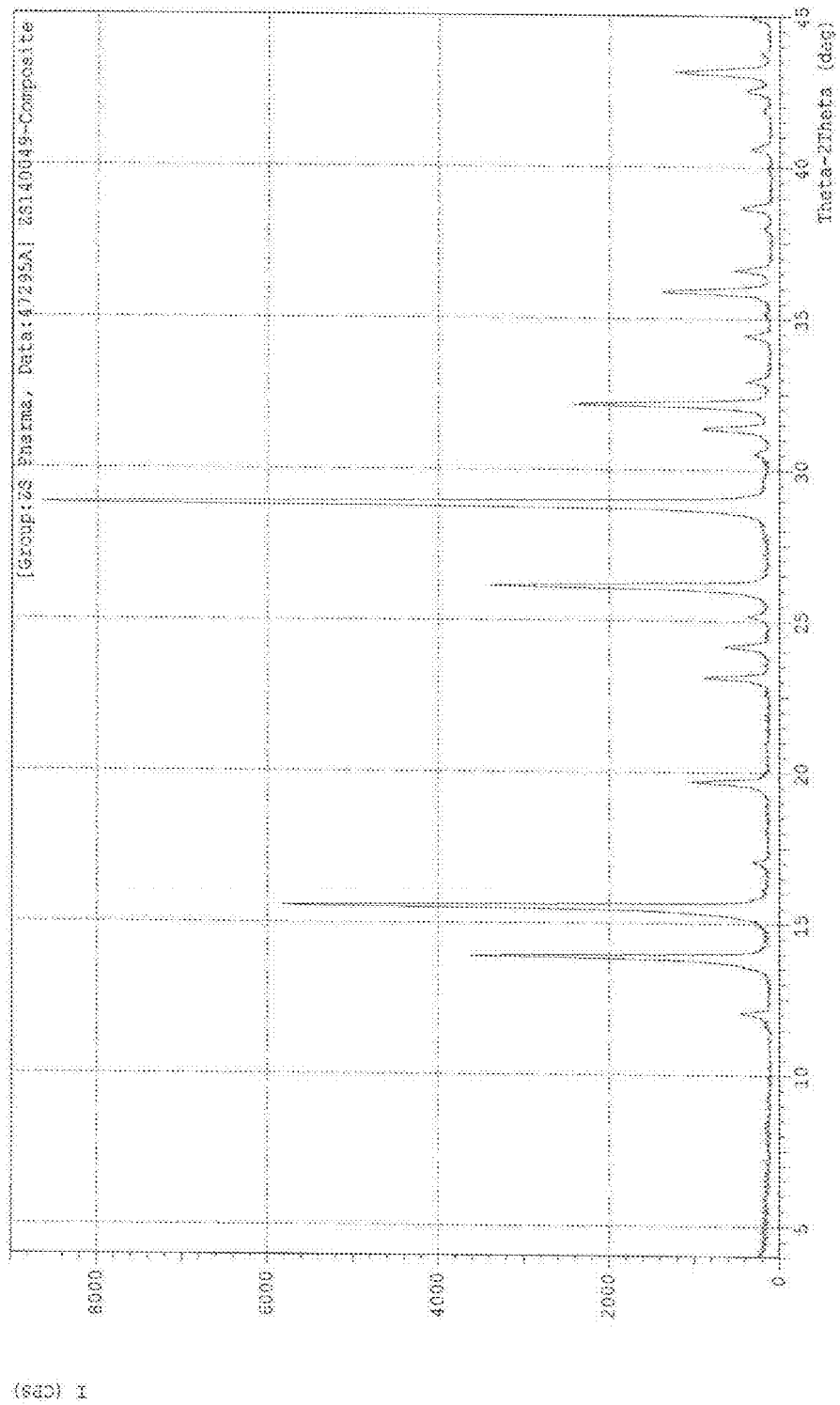
FIG. 5 shows an XRD plot for zirconium silicate prepared according to Example 3.

The particle size distribution of the resulting zirconium silicate prepared in accordance with this example is shown in FIG. 4. The composition exhibited a particle size distribution of about 2% below 3 microns. The XRD plot showed the characteristics for ZS-9, including that the tow highest peaks occur at approximately 15.5 and 28.9, with the highest peak occurring at approximately 28.9. There are undetectable levels of ZS-8 as shown by the absence of please within the range of 5-10 2-theta. See FIG. 5. The resultant zirconium silicate was a white free flowing powder essentially free of debris and particulars. The FTIR spectra exhibited bands at approximately 799 and 917 cm$^{-1}$ which were consistent with previously acceptable lots. The suitable FTIR spectra is shown in the inventors' prior patents. The pH of the resulting material was 9. The measured potassium loading capacity was 3.5 mEq/g. The zirconium content was about 21.7%, the silicon content was approximately 17%, and the sodium content was approximately 7.3%. The moisture content of the final product was 5%.

The level of lead in the final product produced by the above process using colloidal silica was 0.38 ppm, which is a suitable level for the long term administration of this composition.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

Analysis Table 2

|  | Acceptance criteria (ppm) | 500-L Process w/NaAc - Example 2 | | | Example 3 | | |
|  |  | Zirconium Acetate | Sodium Silicate | Zirconium Silicate | Zirconium Acetate | Colloidal Silica | Zirconium Silicate |
| --- | --- | --- | --- | --- | --- | --- | --- |
| Arsenic | 1.5 | ND | ND | ND | ND | 0.06 | ND |
| Cadmium | 0.5 | 0.05 | ND | ND | 0.05 | ND | ND |
| Copper | 300 | ND | 0.09 | 0.57 | 0.05 | 0.08 | 0.19 |
| Iridium | 10 | ND | ND | ND | ND | ND | ND |
| Lead | 0.5 | 0.28 | 0.38 | 1.00 | 0.13 | ND | 0.38 |
| Mercury | 3 | ND | ND | ND | ND | ND | ND |
| Molybdenum | 300 | 0.45 | 0.37 | 0.46 | 0.42 | ND | 1.2 |
| Nickel | 20 | ND | ND | 2.79 | ND | ND | 2.56 |
| Palladium | 10 | ND | ND | ND | ND | ND | ND |
| Platinum | 10 | ND | ND | ND | ND | ND | ND |
| Rhodium | 10 | ND | ND | ND | ND | ND | ND |
| Ruthenium | 10 | ND | ND | ND | ND | ND | ND |
| Vanadium | 10 | ND | ND | ND | ND | 0.33 | ND |

The invention claimed is:

1. A cation exchange composition manufactured by a process of reacting colloidal silica and zirconium acetate at an agitation rate and time sufficient to disrupt silica bonds, wherein the cation exchange composition comprises a zirconium silicate of formula (I):

$$A_p M_x Zr_{1-x} Si_n Ge_y O_m \quad (I)$$

where
- A is a potassium ion, sodium ion, rubidium ion, cesium ion, calcium ion, magnesium ion, hydronium ion or mixtures thereof,
- M is at least one framework metal, wherein the framework metal is hafnium (4+), tin (4+), niobium (5+), titanium (4+), cerium (4+), germanium (4+), praseodymium (4+), terbium (4+) or mixtures thereof,
- "p" has a value from about 1 to about 20,
- "x" has a value from 0 to less than 1,
- "n" has a value from about 0 to about 12,
- "y" has a value from 0 to about 12,
- "m" has a value from about 3 to about 36 and $1 \le n+y \le 12$, wherein the zirconium silicate exhibits a lead content below 0.6 ppm.

2. The composition of claim 1, wherein the lead content ranges from 0.1 to 0.5 ppm.

3. The composition of claim 1, wherein the lead content ranges from 0.3 to 0.5 ppm.

4. The composition of claim 1, wherein the lead content ranges from 0.3 to 0.45 ppm.

5. The composition of claim 1, wherein less than 7% of the particles in the composition have a diameter less than 3 microns.

6. The composition of claim 1, wherein less than 0.5% of the particles in the composition have a diameter less than 1 microns.

7. The composition of claim 1, wherein less than 7% of the particles in the composition have a diameter less than 3 microns, and the sodium content is below 12%.

8. The composition of claim 1, wherein less than 7% of the particles in the composition have a diameter less than 3 microns, and the sodium content is 9% or less.

9. The composition of claim 1, wherein the composition exhibits an XRD diffractogram having the two highest peaks occur at approximately 15.5 and 28.9 degrees 2 theta as obtained from a copper K-alpha radiation source, with the highest peak occurring at 28.9.

10. The composition of claim 1, wherein the pH is from 7 to 9.

11. The composition of claim 1, wherein the potassium loading capacity is between 2.7 and 3.7 mEq/g.

12. The composition of claim 1, wherein the potassium loading capacity is approximately 3.5 mEq/g.

13. A method for treatment of hyperkalemia comprising administering the composition defined in claim 1 to a patient in need thereof.

14. The method of claim 13, wherein the lead content ranges from 0.1 to 0.5 ppm.

15. The method of claim 13, wherein the lead content ranges from 0.3 to 0.5 ppm.

16. The method of claim 13, wherein the lead content ranges from 0.3 to 0.45 ppm.

17. The method of claim 13, wherein less than 7% of the particles in the composition have a diameter less than 3 microns.

18. The method of claim 13, wherein less than 0.5% of the particles in the composition have a diameter less than 1 microns.

19. The method of claim 13, wherein less than 7% of the particles in the composition have a diameter less than 3 microns, and the sodium content is below 12%.

20. The method of claim 13, wherein less than 7% of the particles in the composition have a diameter less than 3 microns, and the sodium content is 9% or less.

21. The method of claim 13, wherein the composition exhibits an XRD diffractogram having the two highest peaks occur at approximately 15.5 and 28.9 degrees 2 theta as obtained from a copper K-alpha radiation source, with the highest peak occurring at 28.9.

22. The method of claim 13, wherein the pH is from 7 to 9.

23. The method of claim 13, wherein the potassium loading capacity is between 2.7 and 3.7 mEq/g.

24. The method of claim 13, wherein the potassium loading capacity is approximately 3.5 mEq/g.

25. The method of claim 13, wherein the administration occurs for more than 5 days.

26. A method of making zirconium silicate of formula (I) comprising:
adding colloidal silica to a reactor, the reactor having a volume of at least 200-L,
reacting the colloidal silica with zirconium acetate at an agitation rate and time sufficient to disrupt silica bonds thereby forming the zirconium silicate of formula (I);

$$A_p M_x Zr_{1-x} Si_n Ge_y O_m \quad (I)$$

where
A is a potassium ion, sodium ion, rubidium ion, cesium ion, calcium ion, magnesium ion, hydronium ion or mixtures thereof,
M is at least one framework metal, wherein the framework metal is hafnium (4+), tin (4+), niobium (5+), titanium (4+), cerium (4+), germanium (4+), praseodymium (4+), terbium (4+) or mixtures thereof,
"p" has a value from about 1 to about 20,
"x" has a value from 0 to less than 1,
"n" has a value from about 0 to about 12,
"y" has a value from 0 to about 12,
"m" has a value from about 3 to about 36 and $1 \leq n+y \leq 12$,
wherein the zirconium silicate has a lead content of less than 0.6 ppm.

27. The method of claim 26, wherein the lead content ranges from 0.1 to 0.6 ppm.

28. The method of claim 26, wherein the lead content ranges from 0.3 to 0.5 ppm.

29. The method of claim 26, wherein the lead content ranges from 0.3 to 0.45 ppm.

30. The composition of claim 1, wherein the agitation rate and time sufficient to disrupt silica bonds is at least 200 rpm for about 20 minutes.

* * * * *